US00PP10715P

United States Patent [19]

Mak

[11] Patent Number: Plant 10,715

[45] Date of Patent: Dec. 8, 1998

[54] ASIATIC HYBRID LILY PLANT NAMED 'LA CENTER'

[76] Inventor: Johan A. Mak, 5595 Halls Ferry Rd., Independence, Oreg. 97351

[21] Appl. No.: 921,125

[22] Filed: Aug. 29, 1997

[51] Int. Cl.[6] ..... A01H 5/00

[52] U.S. Cl. ..... Plt./87.4

[58] Field of Search ..... Plt./87.4

*Primary Examiner*—Howard J. Locker

[57] ABSTRACT

A new variety of a hybrid lily plant bearing upright flowers of excellent form and long persistence, both on the plant and as cut-flowers. The flowers of the new plant are particularly characterized by their deep yellow coloration at the base and the tip, and large orange red mark on the inner half of each tepal. This combination is completely new in the Asiatic hybrid divisions of lilies suited to forcing and to mass commercial cultivation. The variety is resistant to botrytis disease and shows high tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 't Zand, Netherlands, in 1989. The breeding efforts had as their objective the production of large-flowered Asiatic hybrids in yellow coloration with a mark on the inner half of each tepal, flowers in upright position, and tall stem suited to forcing into flower out of season, heretofore unknown in the lily breeding art.

I achieved the desired objective by intercrossing a selected yellow hybrid with a brushmark and an almost clean yellow Asiatic seedlings suited to forcing for year-round use as cut-flowers and carrying the recessive gene for a dark mark on the first half of the flower.

The flowers of my new lily are characterized by lage size and broad-tepalled somewhat "bowl-shaped" form, unusually thick substance, and deep yellow coloration and the orange red mark. It possesses unusually strong, tall stems. In addition, the clone possesses to a high degree desirable characteristics of hybrid vigor. The clone is a good grower and propagator, as observed at 't Zand, Netherlands, and at Salem, Oreg.

My new variety of lily plant has been asexually reproduced by me and under my direction at 't Zand, Netherlands, and at Salem, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive flower coloration with its intense yellow coloration, its dark orange red mark, its orange red buds and its flowers in upright position.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to The Color Chart of the Royal Horticultural Society, published by the Society in 1966.

The Plant

Origin: Seedling.
Seed parent: Petit Urk.
Pollen parent: Selected unnamed yellow Seedling.
Commercial classification: Hybrid Lilium clone.
Horticultural classification: Division 1-A, upright Asiatic hybrid lily, according to the Horticultural Classification of Lilies, Royal Horticultural Society of London.
Form: Single stem, erect and stately.
Height: 80 to 120 cm from bulbs 14 to 18 cm in circumference, provided light levels are adequate; low light levels may cause "stretching".
Color: Green close to R.H.S. C.C. 144D with brown stripes close to R.H.S. C.C. 175A.
Growth: Vigorous and upright.
Foliage quantity: Abundant.
Shape of leaf: Lanceolate (pointed).
Texture: Leathery and glossy.
Color: Green close to R.H.S. C.C. 143 A, lighter on lower side.
Bulb size: Any size, ranging to 25 cm circumference commercially.
Bulb color: White, with flushes of pink or yellow after exposure to light.

The Bud

Form: Obtuse, ovoid, and long.
Size: 8 to 11 cm long and 6 to 8 cm in circumference just prior to opening.
Main color of bud: Close to R.H.S. C.C. 178 A.
Color of midrib: Close to R.H.S. C.C. 178 A with yellow R.H.S. C.C. 15B.
Opening: Bud opens slowly, in response to morning light; this takes about one hour.
Peduncle: Averages 4 to 8 cm, but it may elongate if light levels are too low or if bulbs have been improperly stored prior to forcing. Color is close to R.H.S. C.C. 144 D.

The Flower

Blooming habit: Annually in midseason; flowers once and profusely.
Size: Flowers are medium large-sized, averaging 14.5 to 18 cm in diameter, the outer tepals are 2.5 to 3.50 cm wide, and the inner tepals are 4 to 5.5 cm wide.
Borne: In a single racemic inflorescence producing 9 to 13 flowers from a bulb 14 to 16 cm in circumference.

Shape: Form a somewhat bowl shape by the second day after opening with the tepal tips slightly recurved.
Tepalage: Typical of genus Lilium, with 6 imbricated tepals.
Tepal color: The base of the tepals is R.H.S. C.C. Yellow 12 A, shading into R.H.S. C.C. Orange-Red 42 A at the inner half, and R.H.S. C.C. Yellow 12 A from the orange red mark to the edge and the tip.
Tepal spotting: None.
Tepal longevity: Tepals stay on stems about three weeks.
Pedicel length: Average 6 to 11 cm long.
Pedicel color: Dark green (R.H.S. C.C. 142 B) with dark plum overlay.
Pedicel form: Sturdy and ascending.
Appearance: Flower is shiny.
Disease resistance: The flower and plant are resistant to disease; in particular, they are resistant to viruses and Botrytis blight.
Fragrance: None.
Lasting quality: The flower is long lasting, both on the plant and as a cut-flower.

The Reproductive Organs

Stamens: Arrangement typical of genus Lilium. Six stamens with soft green to palest pink filaments 4 to 7 cm long.
Pollen and anthers (dehisced): R.H.S. C.C. Orange Group 23A.
Pistil: One in number, 4 to 8 cm long.
Stigma: R.H.S. C.C. 187 A.
Characteristics of ovary: Characteristic of genus Lilium.

The Fruit

Fertility: The fruit bears fertile seed.
Shape: Ovoid.
Color at maturity: Soft brown, sometimes overlaid with soft plum.

My new variety of Asiatic hybrid lily most nearly resembles my Asiatic hybrid Petit Urk, but the tepals of the flowers overlap each other while the tepals of the flowers of Petit Urk don't. The mark in the flower of my new Asiatic hybrid is darker and its flowers are more upright.

I claim:

1. A new and distinctive variety of Asiatic hybrid lily plant substantially as herein shown and described, characterized by its high resistance to disease, in particular to viruses and botrytis blight; its vigorous growth and rapid natural propagation; the excellence of its flower form, size, and substance; its versatility both as a garden plant and as a cut-flower producer from pre-cooled bulbs forced under glass out of season; and in particular by its unique upright-facing spotless yellow flowers with dark orange red mark on the inner half of each tepal, a combination unique among Asiatic hybrid lilies suited to forcing and to mass commercial cultivation.

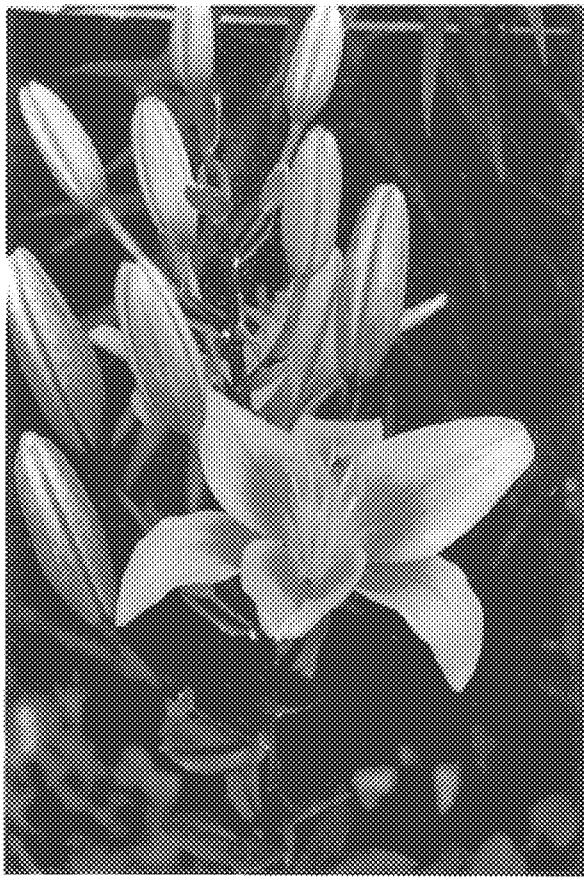

* * * * *